May 10, 1955
YUKIKO OKAZAKI
BOUGAINVILLEA PLANT
Filed June 16, 1953
Plant Pat. 1,393
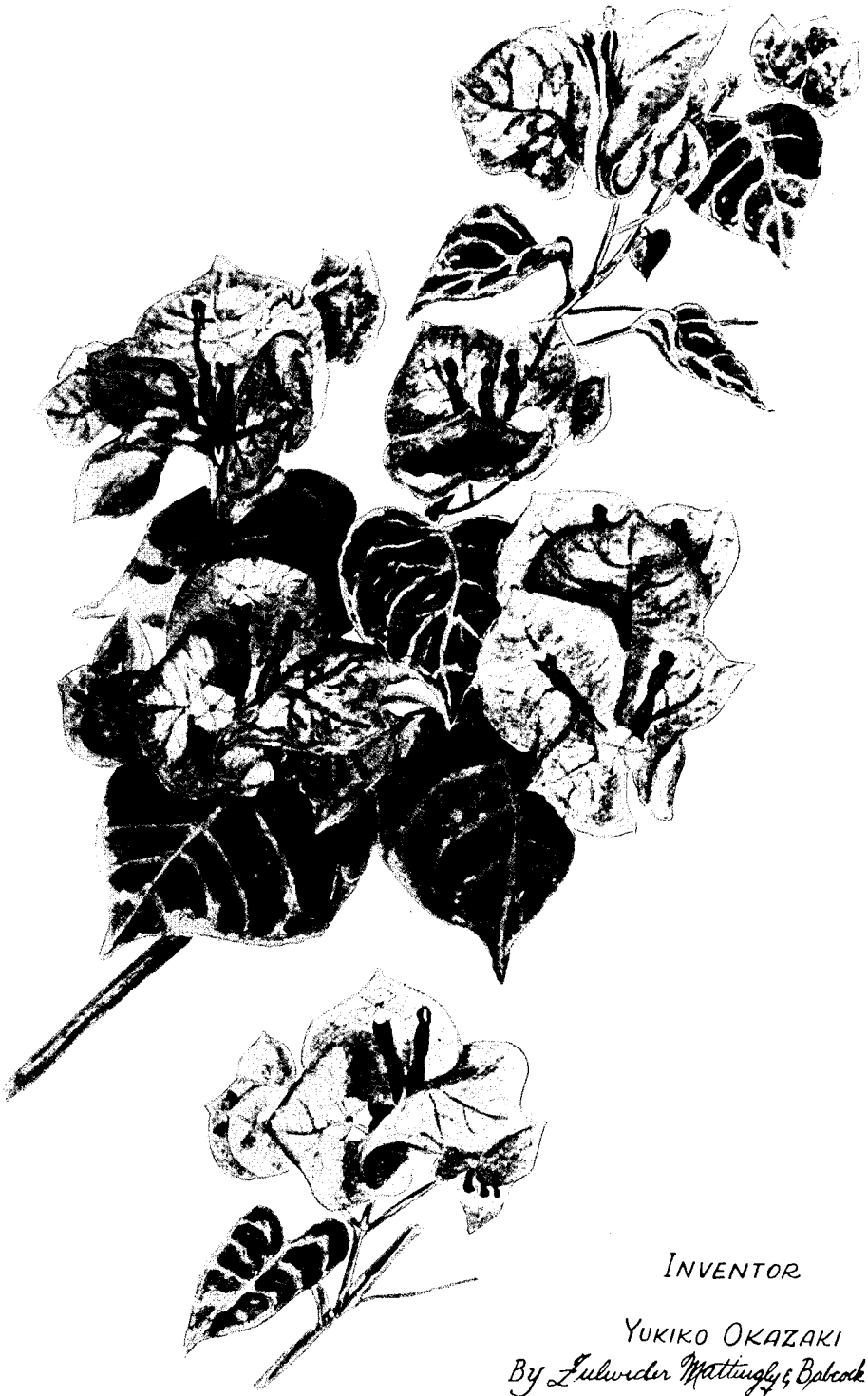
INVENTOR
YUKIKO OKAZAKI
By Fulwider Mattingly & Babcock
Attorneys United States Patent Office Plant Pat. 1,393
Patented May 10, 1955

1,393

BOUGAINVILLEA PLANT

Yukiko Okazaki, Gardena, Calif.

Application June 16, 1953, Serial No. 362,170

1 Claim. (Cl. 47—60)

This discovery relates to a bougainvillea plant of a new and distinct variety that I discovered in Los Angeles, California.

After the discovery of the original parent plant, cuttings were made, and three descendent generations of plants have now been propagated. Hundreds of cuttings have been made, and all of the descendents exhibit the characteristics of the parent plant, thereby showing that the strain is true. The parent plant and the land upon which it grows are owned by me.

The variety was discovered in 1950 as a sport of Bougainvillea Spectabilis v. San Diego Red (unpatented) and differs from that variety and from previously known varieties in that it is more maroon than they are. Whereas the bracts of previous bougainvilleas have generally been purple or a definite red color, the present variety is more to the maroon shade.

When the plant is grown in a greenhouse where it is in subdued light, the blooming period is from March to December, and when the plant is grown outdoors in full sun, its blooming period in Southern California, is from July to December or until the first frost.

The growth of the plant, as to form, size, etc., is similar to the parent plant, San Diego Red, and as mentioned, the unique characteristic of the plant is the color of its bracts. In the following, color references are to "Dictionary of Color" by Maerz and Paul:

Blooming period:

| | |
|---|---|
| In greenhouse | March to December. |
| Outdoors, in full sun | July to December, or until first frost. |

Bud:

| | |
|---|---|
| In greenhouse | 51K12. |
| Outdoors, in full sun | 53L7. |

Mature bracts:

| | |
|---|---|
| In greenhouse | 51K12. |
| Outdoors, in full sun | 53L12. |
| Number of bracts | 3. |
| Size of bracts | Approximately 1¼ inches wide, 1½ inches long. |
| Shape of bracts | Generally oval. |

Blossoms:

Small and comparatively inconspicuous, faint pink color that shades to pale yellow in center of blossom.

Plant:

| | |
|---|---|
| Leaves | 24L5. |
| Stem | 23L1. |

If the plant is grown in a tub or other device so that it can readily be moved, the color of the bracts will change as indicated above when the plant is moved from one condition to another. The bracts exhibit a certain amount of iridescence, and in the drawing, an effort has been made to indicate this iridescence, and also to indicate the appearance of the bracts with a certain amount of light passing through them. The larger spray shows the appearance of a plant that has been grown in full sun, while the smaller spray, at the bottom of the drawing, indicates the appearance of a plant that has been grown in the shade.

The plant has been asexually reproduced at Torrance, Los Angeles County, California, and elsewhere, by cutting a branch from the parent plant, placing the branch in a bed of sand to start the roots, and thereafter when the plant is more mature, transplanting it to a suitable place.

I claim:

A new and distinct variety of bougainvillea plant characterized as to novelty by the maroon color of its bracts and the changing of the color of those bracts when moved between sun and shade, substantially as shown and described.

No references cited.